United States Patent [19]

Reimer

[11] Patent Number: 4,978,225

[45] Date of Patent: Dec. 18, 1990

[54] DETECTION OF ANOMALIES IN TRANSLUCENT MATERIAL BY CANDLING

[75] Inventor: Ernest M. Reimer, St. John's, Canada

[73] Assignee: Canpolar East Inc., St. John's, Canada

[21] Appl. No.: 379,183

[22] Filed: Jul. 13, 1989

[30] Foreign Application Priority Data

Jul. 19, 1988 [CA] Canada ................................ 572411

[51] Int. Cl.$^5$ ............................................ G01N 21/59
[52] U.S. Cl. ...................................... 356/432; 356/53; 356/239
[58] Field of Search .................. 356/53, 239, 432, 440

[56] References Cited

FOREIGN PATENT DOCUMENTS 2605721 8/1977 Fed. Rep. of Germany ........ 356/53

OTHER PUBLICATIONS

Drawing of Scanner marketed by Erwin Sick GmbH of Munich, Germany since 1985.
Drawing of Experimental Equipment, entitled "Foreward and Backward Scatter Imaging Laser Scanning System" assembled by the National Research Council of Iceland in Mar. 1987.
Drawing of Alternative Construction Made by the National Research Council of Iceland in Mar. 1987.
H. E. Power—"The Effect of Various Lighting Conditions on the Efficiency of Candling Cod Fillets for Detection of Parasites"—J.F.R.B. Canada 15(4), 537–542 (1958).
G. H. Valdimarsson et al—"Detection of Parasites in Fish Muscle by Candling Technique"—J. Assoc. Off. Anal. Chem., vol. 68, No. 3 (1985).
K. C. Watts et al—"Search for an Optical Window for Cod Fillets"—an unpublished report for Fisheries and Oceans, Canada (no date).
D. L. Hawley—"Final Report: Fish Parasite Reserach-"—Apr. 14, 1988.

Primary Examiner—Richard A. Rosenberger

[57] ABSTRACT

A candling method for detecting anomalies in translucent material (10) e.g. parasites in fish fillets, comprises directing an illumination beam (Io) of light through the material. It has been discovered that improved results in terms of more reliable detection of anomalies, and the ability to locate such anomalies in thicker samples than has previously been possible, can be obtained by using a beam with a radius no greater than 1 mm and preferably no greater than 0.5 mm. For still better results the beam radius can be reduced to a value no greater than 0.1 mm, and even down to 0.05 mm.

13 Claims, 7 Drawing Sheets

DETECTION OF ANOMALIES IN TRANSLUCENT MATERIAL BY CANDLING

FIELD OF THE INVENTION

This invention relates to a method and apparatus for detecting anomalies in translucent material.

The apparatus has been primarily developed for detecting anomalies in fish fillets, especially the presence of parasites, but it is also useful for detecting bones, blood clots or other foreign objects that would cause the fish fillets to be rejected.

In addition to its use in the inspection of fish fillets, the present invention can also be used for the inspection of other food products, such as eggs, or animal tissues having sufficient translucency, for example relatively thin cuts of meat.

The invention also has medical applications, for example for the inspection of living tissue for foreign objects, tumors or other anomalies, especially in the area of mammography.

BACKGROUND TO THE INVENTION

The art of "candling" is a very old one. The term originally referred to the practice of holding an egg in front of a candle to inspect it for freshness, but the term has since been adopted to more highly technical applications in which objects having at least some degree of translucency are inspected on the basis of light that is directed through the object to the human eye or to some appropriate form of optical detector.

The application of the candling technique to the inspection of fish fillets is known. See for example H. E. Power "The Effect of Various Lighting Conditions on the Efficiency of Candling Cod Fillets for Detection of Parasites" J.F.R.B. Canada 15(4) 537–542 (1958); and G. H. Valdimarsson et al "Detection of Parasites in Fish Muscle by Candling Technique." J. Assoc. Off.ANAL.-CHEM. Vol. 68 No. 3 (1985).

Marine fishes, including commercial species such as cod and herring, are susceptible to infection by a number of parasites. Although a large number of parasites are removed by washing and eviseration, some worms can remain embedded in the filleted portion of a fish. Unless detected and removed, these worms will remain in the flesh and eventually be passed on to the consumer. While the parasites will normally be killed either by cooking or by freezing, they may remain a problem if the fish fillets are eaten raw or are not properly cooked or frozen. In any event, even assuming that the parasites are killed, their presence in the flesh produces an aesthetically unacceptable product. In many countries, inspectors will reject fish products that contains parasites, even though these may have already been killed by freezing.

At present, the commercial detection and removal of fish parasites and other aesthetically unacceptable anomalies such as bone, or blood from bruises, is carried out by a relatively labor intensive method of candling. This involves human inspection of fish fillets as they are passed along a conveyor with a bright light directed to shine through the translucent flesh of the fillet. The method is relatively unreliable, especially if the anomaly is deeply embedded, because of human fatigue and the insufficient ability of the human eye to detect small anomalies in fish fillets that are relatively thick and/or relatively opaque. Because the parasites are less translucent than the flesh of the fish, the parasites can theoretically be detected. However, the attenuation and scattering of the light as it travels through the flesh make the identification of anomalies quite difficult, and it has been determined that the present day technique of candling of cod fillets only detects about 60% of parasites.

Since the early candling techniques were developed, many modifications have been made to the format of the candling table, but it still basically involves a light source beneath a working surface. Studies conducted to define the optimum wavelength of light for the detection of parasites have shown that unfiltered, white light is usually the most effective light source. Recent experiments by K. C. Watts et al (1980) "Search for an Optical Window for Cod Fillets" an unpublished report for Fisheries and Oceans, Canada, have investigated the use of collimated light in the detection of parasites in fish flesh. However, these experiments claimed to find that collimated light was less effective than conventional light sources, and the current recommendation by the Department of Fishery and Oceans, Canada, issued in 1983, is that the most effective candling table is one constructed with a five millimeter thick acrylic sheet with 45% translucency and a light source giving 1500 lux as measured 30 cm above the surface of the table.

A more recent study from Iceland recommends that the light source should be cool white, with a color temperature of 9200° K. Valdimarsson et al in 1985 (cited above) used two 20 watt fluorescent tubes with a conventional candling table. This study suggested that the brightness above the light source should be three times greater than that of the outer field and that the brightness of the outer limit of the visual field should not be more than one tenth the inner field. The overhead light should be at least 500 lux.

Despite all this research and the few improvements that have been made to the candling procedure in recent years, the method remains basically the same and is still very inadequate for a number of reasons. Firstly, the procedure is not convenient for automation and is thus extremely costly in manpower, resulting in increased costs for fish processing and reduced plant productivity. Secondly, even candling with intense light is not totally reliable, especially in relation to relatively thick fillets, e.g. 20 to 25 mm, and also in relation to deeply embedded parasites or other anomalies.

Various workers in this field have suggested the use of other methods, such as ultrasonics, ultraviolet light, X-ray radiation, and acoustic techniques, but none of these methods has proved sufficiently satisfactory to be commercially adopted to date. Optical methods including scanned laser beams have been proposed.

SUMMARY OF THE INVENTION

The principal object of the present invention is to improve the detection of anomalies in translucent material, more particularly anomalies, such as parasites, in fish fillets, in a manner that is more reliable than in the past, and also in a manner that is susceptible to automation.

In particular, it is a further object of the preferred embodiment of the present invention to enable reliable detection of anomalies in translucent material that either has a greater thickness than material with which this has been possible in the past, or has less translucency, or both.

The invention is based on the discovery that the size of the beam constituting the light source has a dramatic effect on performance. None of the prior art methods has recognised this factor. More specifically, it has now been discovered that, while the intensity of the light beam transmitted directly through the material remains substantially independent of the beam radius, the intensity of the light scattered in the material decreases markedly with a decrease in beam radius. Generally speaking, the detection threshold (the point at which it is no longer possible to detect an anomaly) is reached when the intensity of the scattered light becomes equal to or exceeds that of the direct (transmitted) light. Hence it is desirable to make the scattered light intensity as low as possible, which, as indicated above, is a result that has now been found to be attainable by the use of a very small radius illumination beam.

To this end, the invention consists of a candling method comprising directing a beam of light through translucent material for observing an anomaly in such material, characterised in that said beam has a radius no greater than 1 mm.

While the radius of the transmitted beam should be chosen to be no larger than 1.0 mm, it should preferably be no larger than 0.5 mm, or better still, 0.1 mm, and can even be as small as 0.05 mm.

For typical cod fillets having a scattering coefficient TAU (explained below) of about 0.6, the beam radius will normally have to be at least as small as 0.1 mm in order to achieve commercially acceptable detection depths, i.e. of the order of 20 mm or better. However, if the sample under examination has a lower scattering coefficient, say TAU=0.4, a comparable depth of detection can be obtained with a beam radius as large as 1 mm.

Hence, according to the present invention the upper limit of the beam radius has been set at a somewhat arbitrary value of 1 mm, although this value will afford the advantages of the invention only under relatively good conditions, i.e. a relatively low scattering coefficient. For this reason, the preferred value for the beam radius will be 0.5 mm and below, and better still 0.1 mm and below, in order to achieve the full benefit of the present invention under more typical conditions. While the smaller the beam radius, the better the results in terms of the thickness of the sample in which effective detection of an anomaly can be achieved, the practical considerations for generating a very small radius beam at an acceptable cost will normally mean that a radius of 0.05 mm will be about the smallest that it will normally be appropriate to employ.

The invention also provides apparatus for detecting anomalies in translucent material characterised by (a) means for directing an illumination beam of light through said material, said beam having a radius no greater than 1 mm, (b) means for detecting the intensity of an emerging beam of light transmitted through the material from said illumination beam, said detecting means being arranged to be insensitive to light from the illumination beam that is scattered in the material, and (c) means for generating relative movement between said material and said beams in two directions transverse to the direction of travel of said beams and transverse to each other whereby to scan the material with said beams and detect an anomaly in said material by means of a variation in said intensity.

Rendering of the detecting means insensitive to the scattered light is preferably achieved by passing the beam into the detector through an aperture of substantially the same radius as the illumination beam.

DETAILED DESCRIPTION OF THE PREFERRED EMBODIMENTS

Figure 1:
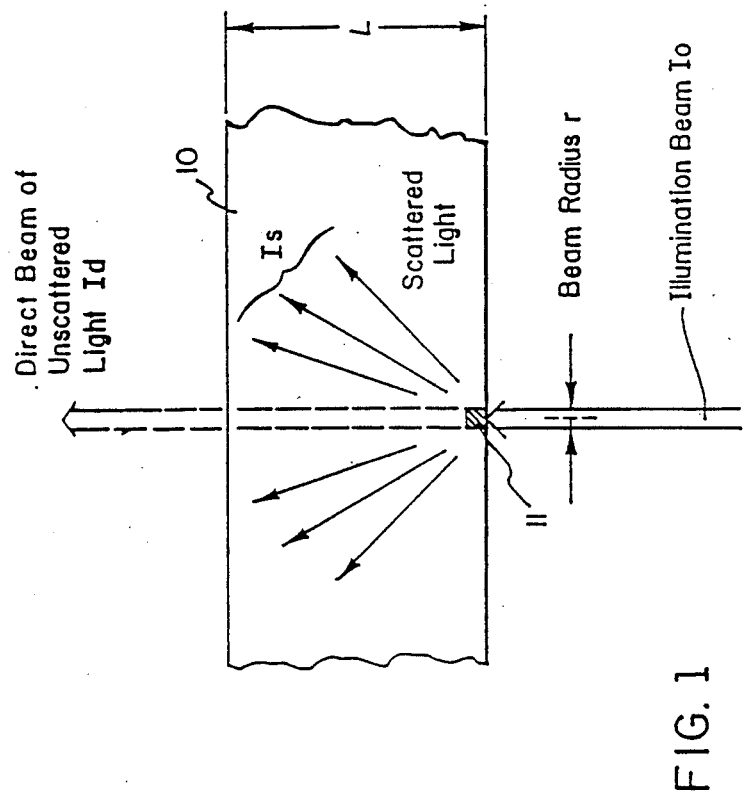
FIG. 1 is a diagram illustrating the scattering of light in a translucent material.

FIG. 1 is an idealized diagram illustrating a mass of translucent material 10 of thickness L, e.g. a fish fillet. An illumination beam Io having a beam radius r is directed against the undersurface of the mass 10 and is assumed to strike a typical small fragment 11 of the material resulting in some of the light being transmitted, i.e. the unscattered direct light Id (having the same beam radius r), and some of the light being scattered as indicated by the arrows Is. Similar action takes place, of course, for each fragment of the material.

The attenuation of the direct beam Id is given by the equation $$Id = Io \, e^{-x}$$

where x is the product of the thickness L and the scattering coefficient TAU.

A typical value of TAU for a cod fillet is 0.6, meaning that 63% of the light is scattered when travelling for a distance of 1.7 millimeter through the material.

Figure 2:
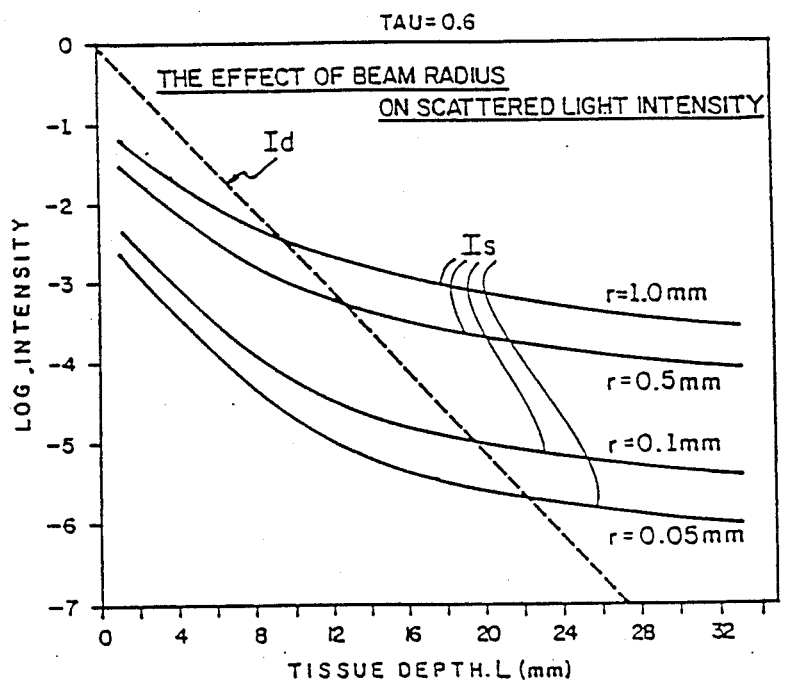
FIG. 2 is a graph indicating the intensity of transmitted and scattered light in translucent material, as a function of its thickness.

FIG. 2 is a graph that illustrates for the condition TAU=0.6 the intensity of the emerging direct beam Id plotted logarithmically against the depth L in millimeters. The broken line Id in FIG. 2 identifies this intensity and will be seen to be straight, in agreement with the above equation. Also, it is independent of the beam radius r. FIG. 2 also shows curves, for different values of the beam radius r, for the intensity of the scattered light Is that reaches the far side of the material 10, i.e. the upper surface in FIG. 1, at the exit point of the direct beam.

In order that a human viewer or an electronic detector be able to distinguish between the direct beam Id and the scattered light Is, as the illumination beam Io is scanned over the translucent material in the two dimensions perpendicular to the depth L in order to detect and locate an anomaly that is more opaque than the remainder of the material, it is necessary that the intensity of Id exceed that of Is. It will be noted from FIG. 2 that, for a value of r of 1.0 mm, for both the beams Io and Id, the curves for Id and Is cross at a depth of about 10 millimeters. This means that under these conditions this depth would constitute the detection threshold, i.e. the maximum thickness for the slab 10 for which detection is assured. This is a relatively unsatisfactory threshold for inspecting most fish fillets, because 90% of commercial fillets will have a thickness greater than 10 millimeters. Typically, most cod fish fillets will have a thickness in the range of 15 to 20 mm, although some fillets may have a thickness up to 25 mm.

FIG. 2 shows how the values of Is are substantially lower for reduced values of the radius r. For example, for a radius r of 0.1 mm detection is possible up to a depth L of almost 20 mm, and there is a still further increase in this value to about 22 mm for the still smaller radius of r=0.05 mm.

Figure 3:
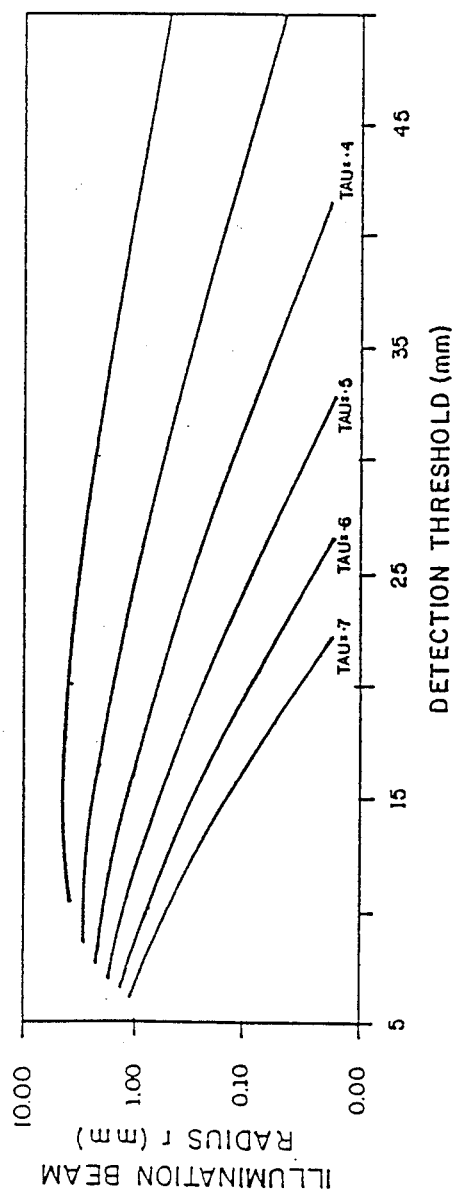
FIG. 3 is another graph showing the detection threshold against the radius of an illumination beam of light for various scattering coefficients.

FIG. 3 illustrates how this detection threshold, i.e. the location at which the value Id exceeds the value Is, varies as a function of the beam radius r for varying values of TAU. It will be noted that, for a given beam radius, the detection threshold increases as the value of TAU decreases. For example, with a beam radius of 0.1 mm, the detection threshold of approximately 20 mm that is achieved when TAU equals 0.6 improves to approximately 25 mm for a value of TAU of 0.5.

The marked improvement achieved by using a small radius beam is also clearly apparent from both FIGS. 2 and 3.

Figure 4:
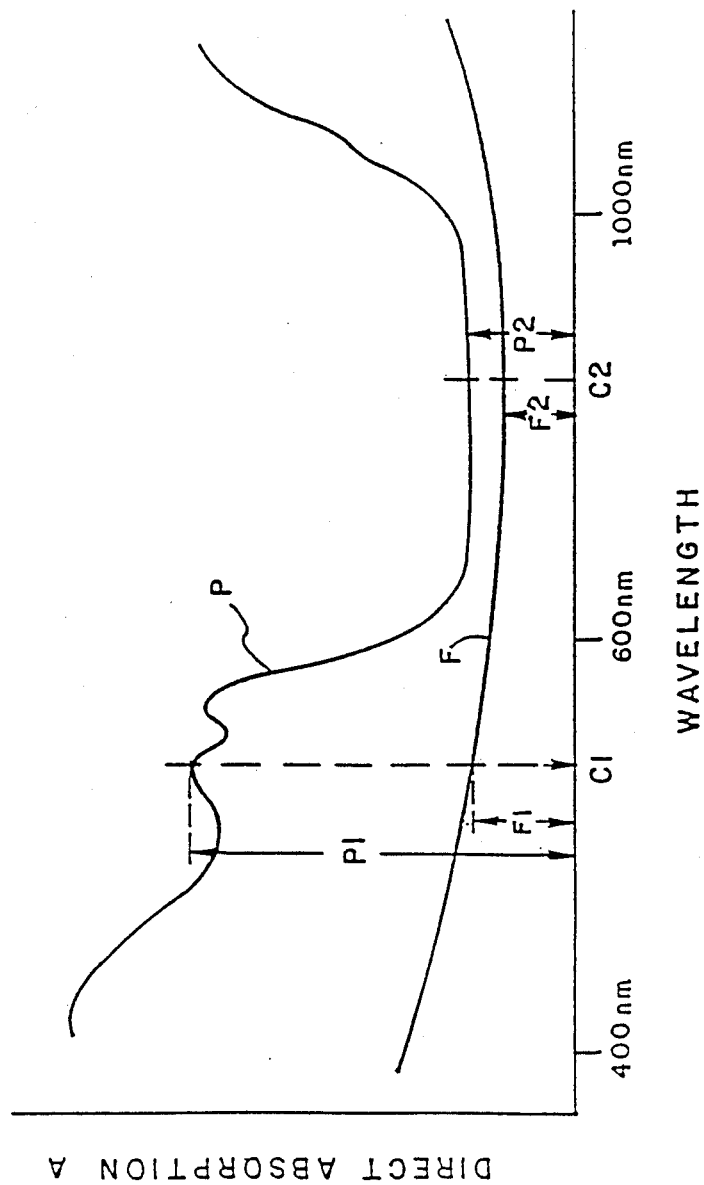
FIG. 4 is a further graph relating the direct absorption of light in fish flesh to the wavelength of such light.

FIG. 4 is a graph illustrating the relationship between the direct absorption A of light by typical fish flesh (curve F) compared with that for a parasite in the fish (curve P), as a function of wavelength in the range 400 nm to 1000 nm. The overall attenuation coefficient is a combination of the scattering coefficient TAU and this direct absorption A. It will be noted that for both curves the least direct absorption A occurs approximately between the visible red wavelength of 600 nm and the near infra red wavelength of 1000 nm, the difference being more pronounced in the case of a parasite (curve P), this being due to absorption by hemoglobin in the parasite. While the region 600-1000 nm would appear to be the best region in which to operate from the viewpoint of the lowest direct absorption A, the visible region between 400 and 600 nm achieves a better contrast between a parasite and the fish flesh. It would normally be inappropriate to use a wavelength below approximately 400 nm, because there would be relatively little penetration of the sample at the ultraviolet frequencies. On the other hand, above 1000 nm the absorption bands for water would tend to interfere with the results. Hence, while the range of 400–1000 nm is preferred, the particular wavelength that is adopted within this range is not critical.

Figure 5:
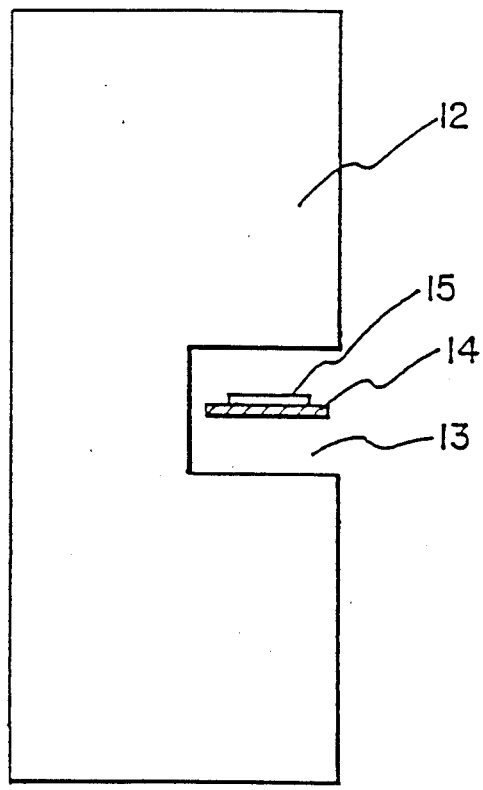
FIG. 5 is an end view of apparatus for carrying out the present invention.
Figure 6:
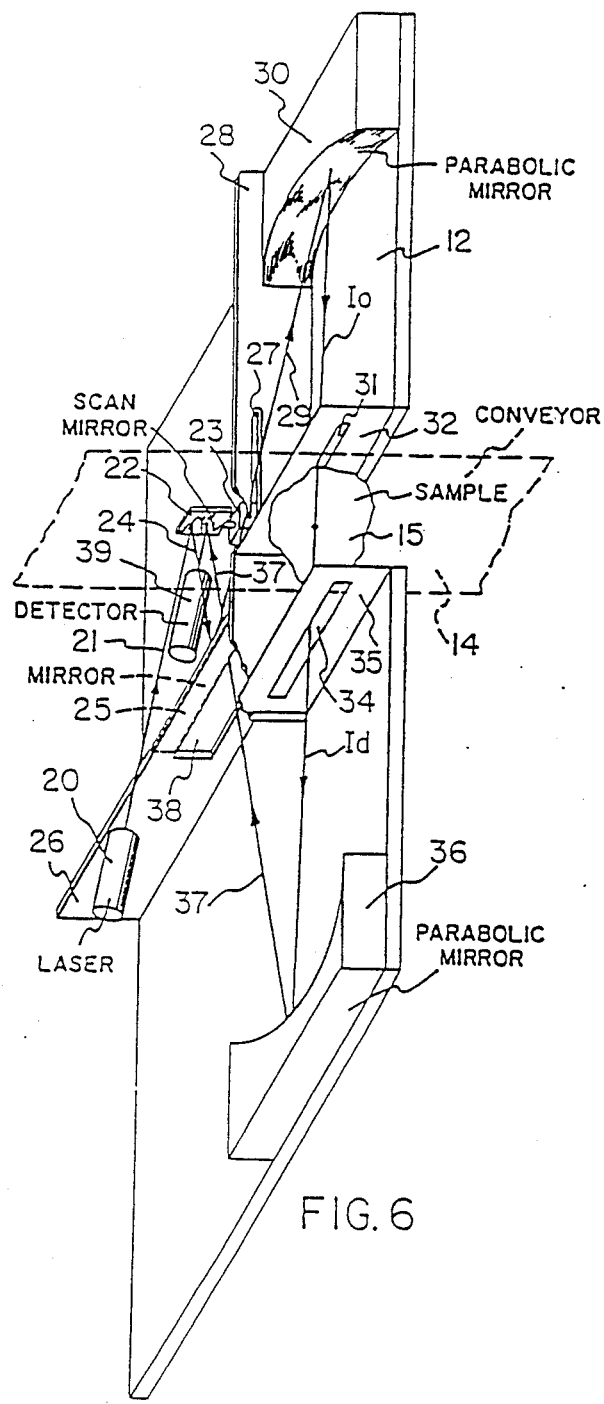
FIG. 6 is an upwardly-looking, perspective, interior view of the apparatus of FIG. 5.

The embodiment described in FIGS. 5 and 6 employs a beam of laser light in the visible portion of the spectrum, e.g. around 500 nm, because such a laser is relatively inexpensive. Moreover, it is not essential to use coherent monochromatic light. A strong beam of white incandescent light with wavelengths spread across the spectrum can theoretically be used. On the other hand, it is generally easier to focus a beam of laser light because it is collimated and monochromatic.

FIG. 5 diagrammically illustrates apparatus for carrying the present invention into practice and consisting of a casing 12 housing the parts shown in FIG. 6. A recess 13 in this casing 12 accommodates a relatively transparent conveyor 14 on which a sample 15, e.g. a fish fillet or other object to be examined, is supported and moved through the apparatus in the direction perpendicular to FIG. 5.

As shown in FIG. 6, the casing 12 serves to house a laser assembly 20 including focusing means whereby there is generated a narrow radius beam 21 in accordance with the present invention. This beam 21 is directed against a scanning mirror 22 that is oscillated by a motor 23 in the known manner. The beam 21 is reflected by the mirror 22 to form a beam 24 which strikes a mirror 25 (shown in broken lines) on the remote side of a structural member 26. The beam 24 is reflected by the mirror 25 through a slot 27 in a further structural member 28 in the form of a beam 29. This beam 29 strikes a parabolic mirror 30 by which it is reflected to form the illumination beam Io that passes through a slot 31 in a structural member 32 forming the upper surface of the recess 13 in which the conveyor 14 and the sample 15 travel. Emerging from the sample 15 is the beam Id which passes through a further slit 34 in a structural member 35 defining the lower surface of the recess 13. This beam Id is reflected by a second parabolic mirror 36 to become a beam 37 that passes through a further slot 38 in the structural member 26 to again strike the scanning mirror 22 and be deflected thereby into a photodetector 39 which includes a focussing lens and a small aperture on the image plane so that the detector only sees the direct beam and substantially none of the scattered light. For this purpose the aperture should have a radius comparable in size to that of the illumination beam Io. By virtue of a slight tilting of one or both of the parabolic mirrors 30, 36, the returning beam 37 strikes the mirror 22 at a location slightly displaced from that of the incoming beam 21 to avoid interference between them.

Scanning in the X direction, namely in the length direction of the conveyor 14 is achieved by the travel of this conveyor, while scanning in the Y direction, i.e. transverse both to the direction of travel of the conveyor 14 and to the direction of the beam Io, is achieved by the oscillation of the scanning mirror 22.

While the particular arrangement shown in FIG. 6 is not essential, in that separate scanning mirrors can be used for the ingoing and outgoing beams, and indeed many variations can be built into the optical system, the illustrated arrangement is preferred because it avoids the difficulty of synchronizing the movement of two mirrors. Using the same side of the same mirror for deflecting the two beams minimizes the opportunity for error.

If desired, the laser light can be modulated, with corresponding modulation in the detector 39. This would avoid the detector seeing ambient light.

If it is desired to know the exact location of the anomaly in three dimensions, the beam arrangement can be duplicated, using two beams simultaneously striking the sample at slightly different angles. In this case, the parabolic mirrors would require to be parabolic in three dimensions rather than in the two dimensions shown.

While it has been assumed that the beam will normally be circular, it need not necessarily be of this shape. Hence, in referring herein to the beam "radius", it is intended to refer to half the major dimension of the beam if such shape is other than circular. In the case of a square beam the value of the "radius" would be half the diagonal dimension, and in the case of a beam having a rectangular cross section, the "radius" would be half the major dimension.

Figure 7:
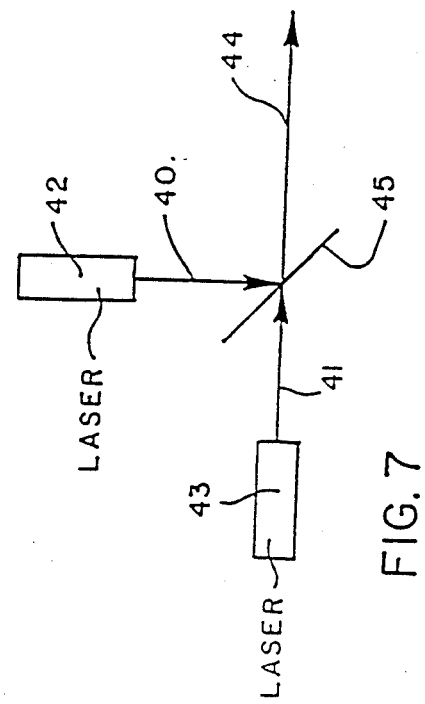
FIG. 7 is a fragmentary view of a modification.

A modification shown in FIG. 7 employs two beams 40, 41 of different colours from respective lasers 42, 43, that are combined into a single beam 44 by means of a mirror 45 that reflects the colour of the beam 40 and transmits the colour of the beam 41, a similar splitting arrangement being provided downstream of the sample for feeding into two detectors (not shown). Such an arrangement reduces clutter and helps to distinguish between the absorption characteristics of the anomaly (parasite) and the fish flesh, as demonstrated in FIG. 4. For example, at colour C1 the absorption by a parasite is P1, whereas at colour C2 it is P2. The corresponding values for the fish flesh are F1 and F2. Since P1-P2 is relatively large, whereas F1 -F2 is much smaller, the effect is that clutter produced by variations in the absorption of light by the fish flesh due, for example, to variations in its translucency or to small pieces of bone or areas of blood or other very minor and acceptable anomalies, has relatively little effect on the readings. Such reduction of clutter improves the machine readability of the image.

What is claimed is:

1. A candling method for inspecting translucent material for anomalies, comprising
   (a) directing an illumination beam of light through said material while scanning said beam over a surface of the material, whereby to generate a correspondingly scanned transmitted beam of light emerging from another surface of the material, and
   (b) observing said emerging beam while excluding light from the illumination beam that is scattered in the material, whereby to detect variations in the intensity of said emerging beam indicative of said anomalies,
   (c) wherein said beams have a radius no greater than 0.1 mm.

2. The method of claim 1, wherein said radius is approximately 0.05 mm.

3. The method of claim 1, wherein said material is fish flesh.

4. The method of claim 1, including the step of modulating said illumination beam to avoid interference from ambient light.

5. The method of claim 1, including the step of employing light of two different frequencies in said illumination beam whereby to detect said variations in intensity at both said frequencies for the reduction of clutter arising from minor, acceptable anomalies.

6. Apparatus for detecting anomalies in translucent material, comprising
   (a) means for directing an illumination beam of light through said material, said beam having a radius no greater than 0.1 mm.
   (b) means for detecting the intensity of an emerging beam of light transmitted through the material from said illumination beam, said detecting means being arranged to be insensitive to light from the illumination beam that is scattered in the material, and
   (c) means for generating relative movement between said material and said beams in two directions transverse to the direction of travel of said beams and transverse to each other whereby to scan the material with said beams and detect an anomaly in said material by means of a variation in said intensity.

7. Apparatus according to claim 6, wherein said radius is approximately 0.05 mm.

8. Apparatus according to claim 6, wherein aperature means are associated with said detecting means for restricting the radius of the beam received by said detecting means to substantially the same as the radius of the illumination beam.

9. Apparatus according to claim 6, wherein said means for generating relative movement includes a conveyor for supporting said material and moving it relative to the beams.

10. Apparatus according to claim 6, wherein said means for generating relative movement includes an oscillating mirror having a surface reflecting both the illumination beam and the emergent beam for simultaneously scanning both said beams relative to the material.

11. Apparatus for detecting anomalies in translucent material, comprising
    (a) means for directing an illumination beam of light through said material, said beam having a radius no greater than 1 mm,
    (b) means for detecting the intensity of an emerging beam of light transmitted through the material from said illumination beam, said detecting means having aperture means for restricting the radius of the beam received by said detecting means to substantially the same as the radius of the illumination beam to cause said detecting means to be insensitive to light from the illumination beam that is scattered in the material, and
    (c) means for generating relative movement between said material and said beams in two directions transverse to the direction of travel of said beams and transverse to each other whereby to scan the material with said beams and detect an anomaly in said material by means of a variation in said intensity,
    (d) said means for generating relative movement including an oscillating mirror having a surface reflecting both the illumination beam and the emerging beam for simultaneously scanning both said beams relative to the material.

12. Apparatus according to claim 11, wherein said means for directing an illumination beam of light through the material comprise
    (e) a scanning mirror for reflecting the illumination beam,
    (f) a first fixed mirror for receiving the reflected illumination beam and generating a further reflected beam,
    (g) a first parabolic mirror for receiving the further reflected beam and directing a still further reflected beam through the material,
    (h) a second parabolic mirror for receiving the emerging beam from the material for generating a fourth reflected beam and directing said fourth beam onto said scanning mirror for reflection thereby to the detecting means.

13. Apparatus according to claim 12, wherein said radius is no greater than 0.1 mm.

* * * * *